US00PP26202P3

(12) United States Plant Patent
Carruth

(10) Patent No.: US PP26,202 P3
(45) Date of Patent: Dec. 15, 2015

(54) MINIATURE ROSE PLANT NAMED 'WEKWIBYPUR'

(50) Latin Name: *Rosa hybrida*
Varietal Denomination: WEKwibypur

(71) Applicant: Early Morning LLC, Pomona, CA (US)

(72) Inventor: Thomas F. Carruth, Altadena, CA (US)

(73) Assignee: Early Morning, LLC, Pomona, CA (US)

( * ) Notice: Subject to any disclaimer, the term of this patent is extended or adjusted under 35 U.S.C. 154(b) by 243 days.

(21) Appl. No.: 13/998,629

(22) Filed: Nov. 18, 2013

(65) Prior Publication Data

US 2015/0143590 P1 May 21, 2015

(51) Int. Cl.
*A01H 5/02* (2006.01)

(52) U.S. Cl.
USPC ..... Plt./123

(58) Field of Classification Search
USPC ..... Plt./123, 116, 101
See application file for complete search history.

(56) References Cited

U.S. PATENT DOCUMENTS

PP16,623 P3 6/2006 Carruth
PP18,554 P2 3/2008 Carruth

*Primary Examiner* — Susan McCormick Ewoldt
*Assistant Examiner* — Karen Redden
(74) *Attorney, Agent, or Firm* — McKee, Voorhees & Sease, PLC

(57) ABSTRACT

A new variety of Miniature rose suitable for garden decoration, having flowers of black purple coloration with a white eyezone.

1 Drawing Sheet

Classification: The present invention relates to a new *Rosa hybrida* plant.

Variety denomination: The new plant has the varietal denomination 'WEKwibypur'.

BACKGROUND OF THE INVENTION

This invention relates to a new and distinct variety of Miniature Rose. It has as its seed parent the variety known as 'WEKisosblip' (U.S. Plant Pat. No. 18,554) and a non-disseminated seedling of my creation as its pollen parent with the following genetic origin (seedling×Baby Love)×Night Owl.

SUMMARY OF THE INVENTION

Among the features which distinguish the new variety from other presently available and commercial rose cultivars known to the inventor are the following combinations of characteristics: its unusual black purple flower coloration with a white eyezone on the upper and under surface of the petals, its strong clove to spicy fragrance and its many stipitate glands on the surface of the bud. The plant has a bushy upright growing habit, suitable for outdoor garden decoration.

Asexual reproduction of the new variety by budding and cuttings as performed in Kern County and Pomona, Calif., shows that the foregoing and other distinguishing characteristics come true to form and are established and transmitted through succeeding asexual propagations. 'WEKwibypur' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKisosblip', by the following combination of characteristics: whereas 'WEKwibypur' bears small sized flowers (about 4.2 to about 5.8 cm. in diameter) of black purple coloration with a white eyezone, 'WEKisosblip' bears significantly larger flowers (about 6.7 to about 10.0 cm. in diameter) of red-purple with a lavender eye coloration. The new variety is classified as a Miniature rose with a bushy upright low to medium height growing habit (about 66 to about 92 cm. in height), whereas the seed parent is classified as a Grandiflora rose with an upright somewhat spreading significantly taller growing habit (about 110 to about 130 cm. in height).

The new variety may be distinguished from its pollen parent, a non-disseminated seedling of my creation, by the following combination of characteristics: whereas 'WEKwibypur' bears double flowers (about 23 to 32 petals) of black purple coloration with a white eyezone, the non-disseminated seedling bears semi-double flowers of dark red coloration with significantly lesser petalage (about 14 to 22 petals). The new variety is classified as a Miniature rose with a bushy upright low to medium height growing habit (about 66 to about 92 cm. in height), whereas the pollen parent is classified as a Shrub rose with a rounded somewhat spreading significantly taller growing habit (about 95 to about 115 cm. in height).

COMPARISON WITH THE CLOSEST COMMERCIALLY AVAILABLE CULTIVAR

The new variety may be distinguished from its closest commercially available cultivar, 'WEKfabpur' (U.S. Plant Pat. No. 16,623) by the following combination of characteristics: whereas 'WEKwibypur' bears small sized flowers (about 4.2 to about 5.8 cm. in diameter) with double petalage (about 23 to 32 petals), 'WEKfabpur' bears significantly larger flowers (about 5.3 to about 7.4 cm. in diameter) with lesser petalage (about 18 to 24 petals).

BRIEF DESCRIPTION OF ILLUSTRATION

The accompanying photograph illustrates the new variety and shows the flowering thereof from bud to full bloom depicted in color as nearly correct as it is possible to make in a color illustration of the character.

Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety sometimes bears its flowers singly, usually in clusters of two to six per stem. Flowers may be borne in regular somewhat flat to rounded clusters on strong short to medium length stems (about 13 to about 33 cm.). Outdoors, the plant blooms abundantly and nearly continuously during the growing season. The flowers have a strong clove to spicy fragrance.

BUD

The peduncle is about 1.7 to about 4.4 cm. in length, of average caliper (about 0.2 to about 0.3 cm. in diameter), and usually erect. It is moderately smooth, with some stipitate glands and few hairs. Peduncle color is between 146B and 146C often moderately suffused, especially on the side exposed to the sun, with between 183B and 187B.

Before the calyx breaks, the bud is about 0.6 to about 1.1 cm. in diameter at the widest point, about 0.7 to about 1.0 cm. in length, and pointed to somewhat ovoid in shape. The surface of the bud bears between 5 to 9 foliaceous appendages and many stipitate glands, usually with slender entire foliaceous parts extending beyond the tip of the bud about ½ or more of its length. Bud color is between 146B and 144A sometimes lightly suffused, especially on the side exposed to the sun, with between 183B and 187B.

The sepals are about 1.8 to about 2.9 cm. in length and about 0.5 to about 0.6 cm. in width at the widest point. The outer surface color of the sepal is between 146B and 144A sometimes lightly suffused, especially on the side exposed to the sun, with between 183B and 187B. The inner surface color of the sepal is near 147D broadly bordered by near 138B. The inner surface of the sepal is covered with fine wooly tomentum; sepal margins are lined with some stipitate glands and hairs.

The receptacle of the flower is of somewhat long length (about 0.4 to about 0.5 cm.) and heavy in caliper for the class (about 0.5 to about 0.6 cm. in diameter). The receptacle is urn-shaped in form. Its surface is smooth with few hairs and stipitate glands and with somewhat thick fleshy walls. The receptacle color is between 146B and 144A sometimes moderately suffused, especially on the side exposed to the sun, with between 183B and 187B.

As the petals open (after the calyx breaks), the bud is about 1.5 to about 2.1 cm. in diameter at the widest point, about 1.1 to about 1.5 cm. in length, and somewhat flat-topped to ovoid in form. The color of the under surfaces of the newly opened petals is between 64A and 64B often heavily suffused with between 187A and 79A. At the point where the petal attaches, there is a very large zone of between 154C and 1C. The color of the upper surfaces of the newly opened petals is between 64A and 64B quickly suffusing over the majority of the petal with between darker than 187A and 79A. At the point where the petal attaches, there is a moderately large zone of between 154C and 1C.

BLOOM

When fully open, the bloom ranges from about 4.2 to about 5.8 cm. in diameter. Petalage is double with about 23 to 32 petals and about 3 to 10 petaloids irregularly arranged. When partially open, the bloom form is moderately ovoid to cupped and the petals are loosely spiraled to cupped with petal edges somewhat reflexed outward. When fully open, the bloom form and the petals are more flat to somewhat cupped with petal edges moderately rolled outward.

PETALS

The substance of the petals is moderately heavy and of medium thickness, with upper surfaces very velvety and under surfaces slightly shiny to matte. The petals are about 1.5 to about 2.2 cm. in length and about 0.9 to about 2.3 cm. in width at the widest point. Petal margins are usually entire.

The outer petals are broadly obovate in shape with rounded to sometimes slightly mucronate apices. The inner petals are somewhat obovate to oblanceolate in shape with rounded to sometimes slightly mucronate apices and sometimes slightly notched with one to two notches.

Petaloids are about 0.6 to about 1.8 cm. in length and about 0.3 to about 0.9 cm. in width at the widest point. Petaloids are irregularly shaped somewhat oblanceolate to subulate with rounded apices.

NEWLY OPENED FLOWER

The under surface color of the outer, intermediate and inner petals is between 70A and 72B quickly suffusing over the majority of the petal with between 187A and as dark as 79A. At the point where the petal attaches, there is a very large zone of between 4D and 155B. The color of the upper surface of the outer, intermediate and inner petals is between 70A and 72B quickly suffusing over the majority of the petal with between 187A and as dark as 79A. At the point where the petal attaches, there is a moderately large zone of between 4D and 155B.

Sometimes, on the upper surface of the inner petals, the zone of between 4D and 155B in coloration will irregularly extend up into the midrib of the petal.

The under and upper surface colors of the petaloids are similar in coloration to the upper and under surfaces of the intermediate and inner petals.

The general tonality of the newly opened flower is between 187A and as dark as 79A with a moderately large eyezone of between 4D and 155B.

THREE-DAY-OLD FLOWER

The under surface color of the outer, intermediate and inner petals is near 77A quickly suffusing over the majority of the petal with between 79B and as dark as 79A. At the point where the petal attaches, there is a very large zone of between 155C and 155B. The color of the upper surface of the outer, intermediate and inner petals is near 77A quickly suffusing over the majority of the petal between 79B and as dark as 79A. At the point where the petal attaches, there is a moderately large zone of between 155A and 155B.

Sometimes, on the upper surface of the inner petals, the zone of between 155A and 155B in coloration will irregularly extend up into the midrib of the petal.

The under and upper surface colors of the petaloids are similar in coloration to the upper and under surfaces of the intermediate and inner petals.

The general tonality of the three-day-old flower is between 79B and as dark as 79A with a moderately large eyezone of between 155A and 155B.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 85) and are arranged regularly about the pistils; a few are mixed with petaloids. The filaments are of somewhat short to medium length (about 0.2 to about 0.7 cm.) most with anthers. Filaments are between 10B and 11B in color sometimes moderately suffused with between 53B and 53C. The anthers are somewhat small for the class and all open approximately at the same time. Anther color when immature is near 17A. Anther color at maturity is near 166A. Pollen is moderately abundant and near 16C in color.

FEMALE REPRODUCTIVE ORGANS

Pistils vary in number (average about 50). The styles are moderately even, of short length (about 0.2 to about 0.3 cm.), somewhat thin to average in caliper and moderately bunched. Stigma color is between 163D and 16B. Style color is near 46A. Ovaries are usually all enclosed in the calyx.

Hips have not been observed to date on this variety when grown in Pomona, Calif.

FOLIAGE

The compound leaves are usually comprised of three to seven leaflets and are borne abundantly. The five-leaflet leaves are about 7.3 to about 12.6 cm. in length and about 5.8 to about 7.5 cm. in width at the widest point, moderately heavy to somewhat crisp in texture, and glossy in finish on the upper side and somewhat semi-glossy to matte in finish on the underside. The leaves have a pinnate venation pattern. The terminal leaflets are about 2.7 to about 5.0 cm. in length and about 1.9 to about 2.5 cm. in width at the widest point, shaped oval to somewhat obovate with moderately acute to somewhat acuminate apices and rounded bases. Their margins are usually simply serrate.

The upper surface color of the mature leaf is between 139A and 137A. The under surface color of the mature leaf is between 137B and 146A. The under and upper colors of the leaf veins on the mature leaf are similar in coloration to the upper and under surfaces colors of the mature leaf. The upper surface color of the young leaf is between 139A and 137A, sometimes lightly suffused with between 183D and 178B. The under surface color of the young leaf is between 137C and 146B, sometimes lightly suffused with between 183D and 178B. The under and upper colors of the leaf veins on the young leaf are similar in coloration to the upper and under surfaces colors of the young leaf.

The rachis is average in caliper and moderately rough. The upper side is moderately grooved with some hairs and stipitate glands on the edges of the grooves. The under side of the rachis is moderately rough with some hairs, few stipitate glands and few very small prickles. The rachis color is near 146C on the underside and near 137A on the upper side.

The stipules are about 1.2 to about 1.7 cm. in length and somewhat narrow to medium in width (about 0.2 to about 0.3 cm.) with medium to long straight points that usually turn out at an angle of more than 45 degrees. The under and upper surface color of the stipule is between 137A and 139A.

The petiole is average in caliper and smooth. The upper side is moderately grooved with some hairs and stipitate glands on the edges of the grooves. The under side of the petiole is smooth with few hairs. The petiole is about 0.1 to about 0.2 cm. in length and about 0.1 cm in width at the widest point. The petiole color is near 146C on the underside and near 137A on the upper side.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has a bushy upright low to medium height growing habit (about 66 to about 92 cm. in height and about 80 to about 105 cm. spread at the widest point), with very full branching. It displays moderately vigorous growth and the canes are of medium caliper for the class (about 0.8 to about 1.2 cm. in width at the widest point).

The color of the major stems is between 147C and 138B. They bear few large prickles that are about 0.5 to about 0.7 cm. in length. The large prickles are almost straight, angled slightly downward with a medium length moderately narrow oval base; prickle color is between 164A and 165B. The major stem bears few small prickles of similar shape and coloration.

The color of the branches is between 138A and 146B. They bear few large prickles which are of similar size and shape to the large prickles on the major stems; prickle color is near 161A. The branches bear few small prickles of similar shape and coloration.

The color of the new shoots is between 138A and 146B often moderately suffused, especially on the side exposed to the sun, with between 183B and 178A. They bear few large prickles which are of similar size and shape to the large prickles on the major stems; prickle color is near 162A sometimes lightly suffused with between 183B and 178A. The shoots bear few small prickles of similar shape and coloration.

I claim:

1. A new and distinct Miniature rose plant of the variety substantially as described and illustrated herein.

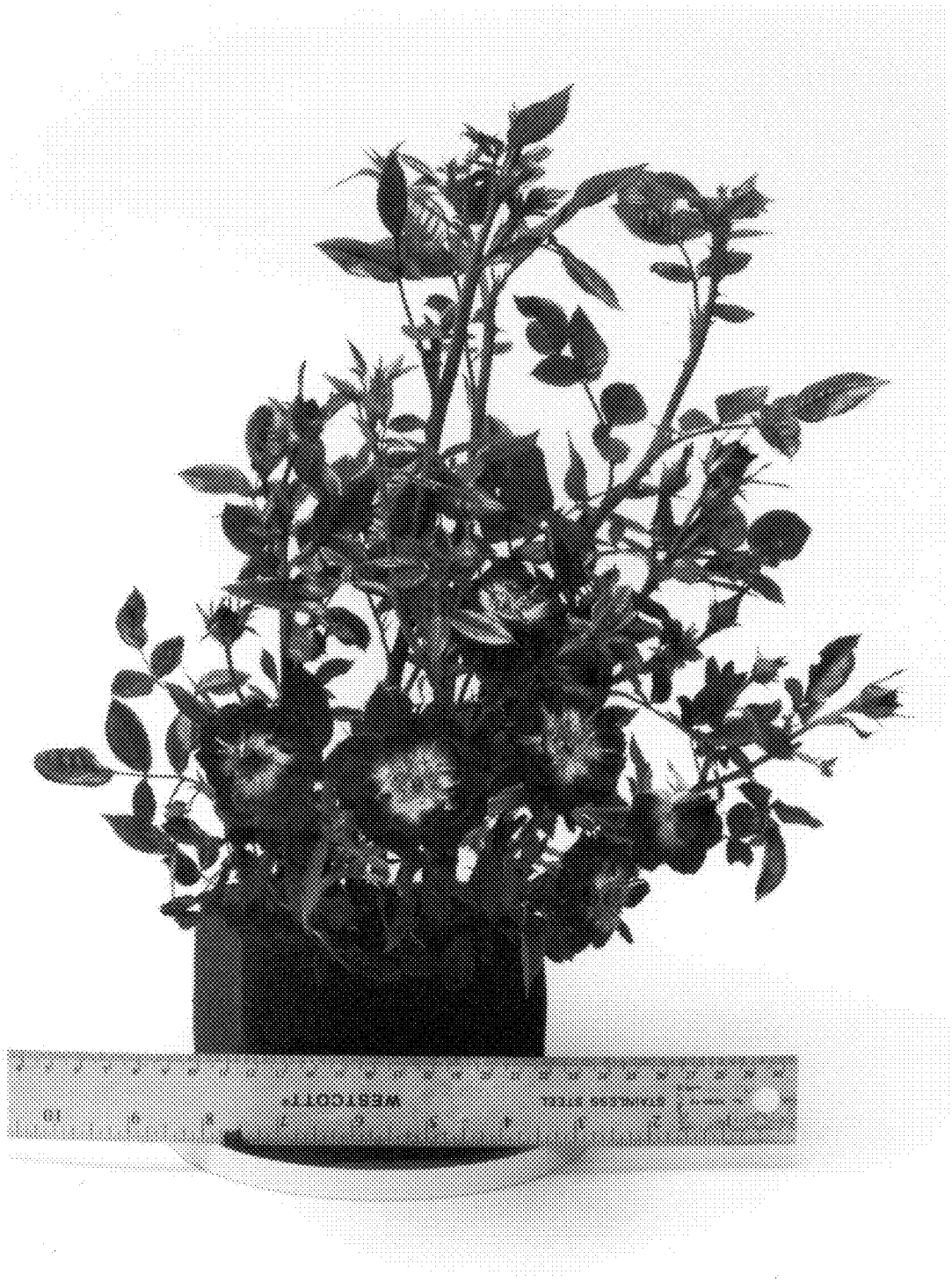

* * * * *